United States Patent
Vuilleme

(10) Patent No.: US 6,613,275 B1
(45) Date of Patent: Sep. 2, 2003

(54) NON-PRECIOUS DENTAL ALLOY

(75) Inventor: Nicolas Vuilleme, Yverdon (CH)

(73) Assignee: Metalor Technologies SA, Neuchatel (CH)

( * ) Notice: Subject to any disclaimer, the term of this patent is extended or adjusted under 35 U.S.C. 154(b) by 0 days.

(21) Appl. No.: 10/199,722

(22) Filed: Jul. 19, 2002

(51) Int. Cl.$^7$ ................................................ C22C 19/07
(52) U.S. Cl. .................. 420/439; 420/436; 420/587; 420/588; 420/589; 148/425; 148/442
(58) Field of Search ................................ 420/435, 436, 420/439, 587, 588, 589; 148/425, 442

(56) References Cited

U.S. PATENT DOCUMENTS

| | | | | |
|---|---|---|---|---|
| 4,514,359 A | | 4/1985 | Andrews | 420/436 |
| 4,911,762 A | * | 3/1990 | Steinemann | 75/245 |
| 5,200,002 A | * | 4/1993 | Hilzinger | 148/304 |
| 2002/0041820 A1 | * | 4/2002 | Prasad | 420/437 |

FOREIGN PATENT DOCUMENTS

| | | | |
|---|---|---|---|
| JP | 58-110633 | * | 7/1983 |

* cited by examiner

*Primary Examiner*—John Sheehan
(74) *Attorney, Agent, or Firm*—Van Tassel & Associates

(57) ABSTRACT

The present invention concerns a non-precious dental alloy, including the following components, with the approximate proportions, in weight, given in %:

gold, between 0.5 and 4,
molybdenum, between 4 and 6,
tungsten, between 2 and 7,
indium, between 0.5 and 4,
gallium, between 0.5 and 4,
tin, between 0 and 4,
titanium, between 0 and 2,
copper, between 0 and 2, the remainder being obtained with a mixture containing approximately 70% cobalt and 30% chromium.

4 Claims, No Drawings

NON-PRECIOUS DENTAL ALLOY

The present invention relates to metal alloys. It concerns, more particularly, a non-precious dental alloy, i.e. including only a small proportion of precious metals (gold, silver . . . ), typically less than 20% in weight.

A metal or metal alloy intended to be used for dental reconstruction, such as crowns or bridges, has to be solid, biocompatible and has to be resistant to tarnishing, oxidization and corrosion. Moreover, it has to be easily conformable in order to manufacture precise parts, by casting or in accordance with any of the common techniques known to those skilled in the art.

For aesthetical reasons, dental prostheses are, today, often covered with a ceramic cap. This poses two main problems. Indeed, not only must the ceramic cap adhere sufficiently to the surface of the alloy, but the two materials must also react in a similar manner to changes in temperature, to avoid creating tensions at their interface. The criterion enabling this latter point to be checked is the thermal expansion coefficient.

Precious alloys, i.e. including a proportion typically greater than 20% in weight of precious metals (gold, silver . . . ), have proved their quality for making such dental reconstructions. However, their high cost has led metallurgists to seek non-precious metals suited to this application. The first satisfactory results were obtained with nickel-based alloys, this metal having then been slowly replaced by cobalt because of allergy problems. But numerous other non-precious elements have to be added to cobalt, in particular chromium and molybdenum in order to satisfy resistance to corrosion and biocompatibility criteria. Examples are presented, in particular, in U.S. Pat. No. 4,514,359. Nonetheless, the additives used make the alloys difficult to work.

The present invention thus proposes a biocompatible non-precious dental alloy, whose thermal expansion coefficient is close to that of the dental ceramics used to cap the alloy, which is resistant to corrosion and tarnishing, easily conformable and inexpensive.

More precisely, the invention concerns a non-precious dental alloy including the following components, with approximate proportions, in weight, given in %:
- gold, between 0.5 and 4,
- molybdenum, between 4 and 6,
- tungsten, between 2 and 7,
- indium, between 0.5 and 4,
- gallium, between 0.5 and 4,
- tin, between 0 and 4,
- titanium, between 0 and 2,
- copper, between 0 and 2, the remainder being obtained with a mixture containing approximately 70% cobalt and 30% chromium.

Preferably, the sum of indium, tin and gallium constitutes at least 1.5% of the alloy, whereas the sum of titanium and copper constitutes at least 0.25%.

In a particularly advantageous manner, the dental alloy according to the invention includes approximately 2% gold, 5% molybdenum, 4% tungsten, 1.2% indium, 2.5% gallium, 1% titanium, 59.3% cobalt and 25% chromium.

The main components of the alloy are cobalt, chromium, molybdenum and tungsten. They are the source of the mechanical, physical, biocompatible and corrosion resistant characteristics of the material. The secondary elements such as gold, indium, gallium, tin, titanium or copper play an important role for the adhesion of a ceramic layer used in reconstruction parts.

Cobalt is the major component, selected for its mechanical qualities, its resistance to corrosion and its low cost.

Chromium and molybdenum further improve the behavior of the alloy against corrosion. They also act by reinforcing the material and influencing its thermal expansion coefficient, in accordance with the requirements necessary for connection to a ceramic part.

Tungsten increases the stability of the alloy's phases at high temperatures. It tends to decrease the hardness of the final material at ambient temperature, which facilitates operations like polishing. Finally, tungsten acts efficiently and significantly as a regulator of the thermal expansion coefficient.

Indium, gallium and, to a lesser extent, tin have similar influences on a cobalt and chromium based alloy: they lower the melting point of the alloy, which facilitates casting operations for shaping the material. They reduce the hardness of the alloy, while increasing and regulating the thermal expansion coefficient.

Titanium and copper, in small quantities, substantially improve the quality of the alloy's adhesion to the ceramic material.

In order to make the alloy, the required quantities of the various components are dissolved so as to form a homogenous alloy, then solidified in a form suited to future use (ingot, powder . . . ). The alloy is then shaped, for example via the lost-wax casting technique.

The alloy may, further, contain traces of manganese, silicon and carbon inherent in the raw materials and resulting from the processes used.

Thus, an alloy containing 2% gold, 5% molybdenum, 4% tungsten, 1.2% indium, 2.5% gallium, 1% titanium, 59.3% cobalt and 25% chromium has the following properties:

Mechanical Properties:
  Tensile Properties:
    Young modulus: 180 000 MPa
    Yield stress (0.2%): 470 MPa
    Ultimate tensile stress: 670 MPa
    Elongation: 8%
  Hardness Properties:
    After casting: 265 Hv5
    After firing: 280 Hv5
Physical Properties:
  Density: 8.4 g/cm$^3$
  Melting range: 1300–1400° C.
  Thermal expansion:
    14.1 (between 25 and 500° C.) $10^{-6}$/° C.
    14.5 (between 25 and 600° C.) $10^{-6}$/° C.
Corrosion Properties:
  Electrochemical analysis, according to the ISO 10271 standard
    Rest potential: −235 mV
    Break potential: 642 mV
  Chemical corrosion, according to the ISO 1562 standard:
    Results below 100 µg/cm$^2$
  Tarnishing, according to the ISO 1562 standard:
    a Good results
Biocompatibility:
  The alloy has successfully passed the cytotoxicity, mutagenicity and sensitivity tests according to the ISO 10993 standard.
Bonding to ceramics:
  The alloy has been successfully tested with the following ceramics
    Ceramco II, from Dentsply; Creation Plus, from Klemadent; Duceram Plus, from Ducera; D.sign and IPS-classic, from Ivoclar; EX-3 from Noritake; Halo and Vintage, from Shofu; Symbiceram and Omega 900, from Vita.

Thus, there is proposed a non-precious dental alloy which perfectly satisfies the mechanical and physical requirements necessary for its use in conjunction with a ceramic cap. Moreover, the material obtained offers particularly satisfactory results in terms of biocompatibility and resistance to tarnishing and corrosion, while being easy to work.

What is claimed is:

1. Non-precious dental alloy including the following components, with the approximate proportions, in weight, given in %:

gold, between 0.5 and 4, molybdenum, between 4 and 6, tungsten, between 2 and 7, indium, between 0.5 and 4, gallium, between 0.5 and 4, tin, between 0 and 4, titanium, between 0 and 2, copper, between 0 and 2, the remainder being obtained with a mixture containing approximately 70% cobalt and 30% chromium.

2. Dental alloy according to claim 1, wherein the sum of the indium, tin and gallium constitutes at least 1.5% of the alloy.

3. Dental alloy according to claim 1, wherein the sum of the titanium, and copper constitutes at least 0.25% of the alloy.

4. Dental alloy according to claim 1, including approximately 2% gold, 5% molybdenum, 4% tungsten, 1.2% indium, 2.5% gallium, 1% titanium, 59.3% cobalt and 25% chromium.

* * * * *